United States Patent
Li et al.

(10) Patent No.: US 8,930,145 B2
(45) Date of Patent: Jan. 6, 2015

(54) LIGHT FOCUSING CONTINUOUS WAVE PHOTOACOUSTIC SPECTROSCOPY AND ITS APPLICATIONS TO PATIENT MONITORING

(75) Inventors: Youzhi Li, Longmont, CO (US); Edward M. McKenna, Boulder, CO (US); Andy S. Lin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1081 days.

(21) Appl. No.: 12/845,198

(22) Filed: Jul. 28, 2010

(65) Prior Publication Data

US 2012/0029829 A1    Feb. 2, 2012

(51) Int. Cl.
| | | |
|---|---|---|
| G01N 33/48 | (2006.01) | |
| A61B 5/05 | (2006.01) | |
| A61B 5/00 | (2006.01) | |
| G01N 21/17 | (2006.01) | |
| A61B 5/1455 | (2006.01) | |

(52) U.S. Cl.
CPC ............ *A61B 5/0059* (2013.01); *A61B 5/0095* (2013.01); *G01N 21/1702* (2013.01); *A61B 5/1455* (2013.01)
USPC ............................................ 702/19; 600/407

(58) Field of Classification Search
USPC ........... 702/19, 22–23, 28, 30, 32, 39–40, 81, 702/84, 127, 138–139, 170–172, 182–183, 702/188–189; 73/584, 587, 632–633, 73/642–643, 645–647, 649, 656; 356/39–41; 600/300–301, 310, 320, 600/323, 332, 407, 425, 437, 476
See application file for complete search history.

(56) References Cited

U.S. PATENT DOCUMENTS

| | | | |
|---|---|---|---|
| 3,638,640 | A | 2/1972 | Shaw |
| 4,714,341 | A | 12/1987 | Hamaguri et al. |
| 4,805,623 | A | 2/1989 | Jöbsis |
| 4,807,631 | A | 2/1989 | Hersh et al. |
| 4,817,623 | A | 4/1989 | Stoddart et al. |
| 4,911,167 | A | 3/1990 | Corenman et al. |
| 4,913,150 | A | 4/1990 | Cheung et al. |
| 4,936,679 | A | 6/1990 | Mersch |
| 4,938,218 | A | 7/1990 | Goodman et al. |
| 4,971,062 | A | 11/1990 | Hasebe et al. |

(Continued)

FOREIGN PATENT DOCUMENTS

| | | |
|---|---|---|
| AU | 732799 | 5/2001 |
| DE | 19640807 | 9/1997 |

(Continued)

OTHER PUBLICATIONS

Meyer et al., Tailoring Ultrasonic Beams with Optoacoustic Holography, 2003, Proceedings of SPIE, vol. 4969, pp. 105-114.*

(Continued)

*Primary Examiner* — Toan Le
(74) *Attorney, Agent, or Firm* — Fletcher Yoder PC (57) ABSTRACT

The present disclosure describes systems and methods that use spatial modulation to focus continuous wave light into a localized region of interest such as an individual blood vessel. In certain embodiments, intensity modulation techniques, such as linear frequency modulation, are used in conjunction with spatial modulation to achieve more precise measurements through otherwise scattering medium. The focused beam of continuous wave light is capable of penetrating several centimeters of tissue to deliver measurements and images associated with individual blood vessels and other discrete vascular components.

25 Claims, 3 Drawing Sheets

(56) References Cited

U.S. PATENT DOCUMENTS

| | | |
|---|---|---|
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,140,989 A | 8/1992 | Lewis et al. |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,349,961 A | 9/1994 | Stoddart et al. |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Keunstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,309,352 B1 | 10/2001 | Oraevsky et al. |
| 6,312,393 B1 | 11/2001 | Abreu |
| 6,353,750 B1 | 3/2002 | Kimura et al. |
| 6,397,091 B2 | 5/2002 | Diab et al. |
| 6,405,069 B1 | 6/2002 | Oraevsky et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,519,376 B2 | 2/2003 | Biagi et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,839,496 B1 | 1/2005 | Mills et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,020,506 B2 | 3/2006 | Fine et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,127,278 B2 | 10/2006 | Melker et al. |
| 7,162,306 B2 | 1/2007 | Caby et al. |
| 7,184,148 B2 | 2/2007 | Alphonse |
| 7,209,775 B2 | 4/2007 | Bae et al. |
| 7,236,811 B2 | 6/2007 | Schmitt |
| 7,254,432 B2 | 8/2007 | Fine |
| 7,263,395 B2 | 8/2007 | Chan et al. |
| 7,272,426 B2 | 9/2007 | Schmid |
| 7,327,463 B2 | 2/2008 | Alphonse |
| 7,373,193 B2 | 5/2008 | Al-Ali et al. |
| 7,447,388 B2 | 11/2008 | Bates et al. |
| 7,483,731 B2 | 1/2009 | Hoarau et al. |
| 7,650,177 B2 | 1/2010 | Hoarau et al. |
| 7,680,522 B2 | 3/2010 | Andershn et al. |
| 7,869,850 B2 | 1/2011 | Hoarau et al. |
| 7,899,510 B2 | 3/2011 | Hoarau |
| 8,060,171 B2 | 11/2011 | Hoarau |
| 8,109,272 B2 | 2/2012 | Baker, Jr. |
| 8,123,695 B2 | 2/2012 | Baker, Jr. |
| 8,145,288 B2 | 3/2012 | Baker, Jr. |
| 8,175,671 B2 | 5/2012 | Hoarau |
| 8,190,224 B2 | 5/2012 | Hoarau |
| 8,190,225 B2 | 5/2012 | Hoarau |

(56) References Cited

U.S. PATENT DOCUMENTS

| | | |
|---|---|---|
| 8,195,264 B2 | 6/2012 | Hoarau |
| 8,233,954 B2 | 7/2012 | Klingt et al. |
| 8,311,601 B2 | 11/2012 | Besko |
| 8,364,220 B2 | 1/2013 | Sandmore |
| 8,396,527 B2 | 3/2013 | Hoarau |
| 8,417,309 B2 | 4/2013 | Price |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0054907 A1 | 3/2005 | Page et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0175540 A1 | 8/2005 | Oraevsky et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0063992 A1 | 3/2006 | Yu et al. |
| 2006/0063993 A1 | 3/2006 | Yu et al. |
| 2006/0064024 A1 | 3/2006 | Schnall |
| 2006/0195028 A1 | 8/2006 | Hannula et al. |
| 2006/0224053 A1 | 10/2006 | Black et al. |
| 2006/0224058 A1 | 10/2006 | Mannheimer |
| 2006/0247501 A1 | 11/2006 | Ali |
| 2006/0253007 A1 | 11/2006 | Cheng et al. |
| 2006/0258921 A1 | 11/2006 | Addison et al. |
| 2007/0015992 A1 | 1/2007 | Filkins et al. |
| 2007/0093702 A1 | 4/2007 | Yu et al. |
| 2007/0197886 A1* | 8/2007 | Naganuma et al. ............ 600/322 |
| 2008/0200781 A1 | 8/2008 | Van Herpen et al. |
| 2008/0296514 A1 | 12/2008 | Metzger et al. |
| 2011/0083509 A1 | 4/2011 | Li et al. |

FOREIGN PATENT DOCUMENTS

| | | |
|---|---|---|
| EP | 0630203 | 12/1994 |
| EP | 0919180 A1 | 6/1999 |
| EP | 1743576 A1 | 1/2007 |
| GB | 2311858 A1 | 10/1997 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 10216115 | 8/1998 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| WO | WO9101678 | 2/1991 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO2005009221 | 2/2005 |
| WO | 2007003952 A2 | 1/2007 |
| WO | WO2007051066 | 5/2007 |
| WO | WO2008149342 | 12/2008 |

OTHER PUBLICATIONS

Kihm et al., Interferometry-Based Optoacoustic Tomography, 2009, Taylor & Francis Group, LLC, pp. 239-250.*

Telenkov et al., Photothermoacoustic Imaging of Biological Tissues: Maximum Depth Characterization Comparison of Time and Frequency-Domain Measurements, Jul./Aug. 2009, Journal of Biomedical Optics, vol. 14(4), 12 pp.*

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

(56) References Cited

OTHER PUBLICATIONS

East, Christine E., et al.; "Fetal Oxygen Saturation and Uterine Contractions During Labor," *American Journal of Perinatology*, vol. 15, No. 6, pp. 345-349 (Jun. 1998).
Hayes, Matthew J., et al.; "Quantitative evaluation of photoplethysmographic artifact reduction for pulse oximetry," *SPIE*, vol. 3570, pp. 138-147 (Sep. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Hayes, Matthew J., et al.; "Artifact reduction in photoplethysmography," *Applied Optics*, vol. 37, No. 31, pp. 7437-7446 (Nov. 1998).
Such, Hans Olaf; "Optoelectronic Non-invasive Vascular Diagnostics Using multiple Wavelength and Imaging Approach," *Dissertation*, (1998).
Todd, Bryan, et al.; "The Identification of Peaks in Physiological Signals," *Computers and Biomedical Research*, vol. 32, pp. 322-335 (1999).
Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.
Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).
Kaestle, S.; "An Algorithm for Reliable Processing of Pulse Oximetry Signals Under strong Noise Conditions," *Dissertation Book*, Lubeck University, Germany (1999).
Goldman, Julian M.; "Masimo Signal Extraction Pulse Oximetry," *Journal of Clinical Monitoring and Computing*, vol. 16, pp. 475-483 (2000).
Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.
Kaestle, S.; "Determining Artefact Sensitivity of New Pulse Oximeters in Laboratory Using Signals Obtained from Patient," *Biomedizinische Technik*, vol. 45 (2000).
Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).
Belal, Suliman Yousef, et al.; "A fuzzy system for detecting distorted plethysmogram pulses in neonates and paediatric patients," *Physiol. Meas.*, vol. 22, pp. 397-412 (2001).
Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.
Jopling, Michae W., et al.; "Issues in the Laboratory Evaluation of Pulse Oximeter Performance," *Anesth Analg*, vol. 94, pp. S62-S68 (2002).
Gostt, R., et al.; "Pulse Oximetry Artifact Recognition Algorithm for Computerized Anaesthetic Records," *Journal of Clinical Monitoring and Computing Abstracts*, p. 471 (2002).
Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).
Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.
Aoyagi, Takuo; "Pulse oximetry: its invention, theory, and future," *Journal of Anesthesia*, vol. 17, pp. 259-266 (2003).
Lee, C.M., et al.; "Reduction of motion artifacts from photoplethysinographic recordings using wavelet denoising approach," *IEEE EMBS Asian-Pacific Conference on Biomedical Engineering*, Oct. 20-22, 2003; pp. 194-195.
Johansson, A.; "Neural network for photoplethysmographic respiratory rate monitoring," *Medical & Biological Engineering & Computing*, vol. 41, pp. 242-248 (2003).
Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).
Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.
Matsuzawa, Y., et al.; "Pulse Oximeter," *Home Care Medicine*, pp. 42-45 (Jul. 2004); (Article in Japanese—contains English summary of article).
Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).
Telenkov, Sergey A., et al.; "Fourier-domain biophotoacoustic subsurface depth selective amplitude and phase imaging of turbid phantoms and biological tissue," *Journal of Biomedical Optics*, 11(4), 044006, Jul./Aug. 2006.
Vellekoop, I.M., et al.; "Focusing coherent light through opaque strongly scattering media," *Optics Letters*, vol. 32, No. 16, Aug. 15, 2007.
Maslov, Konstantin, et al.; "Photoacoustic imaging of biological tissue with intensity-modulated continuous-wave laser," *Journal of Biomedical Optics*, 13(2), 024006, Mar./Apr. 2008.
Vellekoop, I.M., et al.; "Focusing Coherent Light Through Opaque Strongly Scattering Media," Aug. 15, 2007 Optical Society of America, vol. 32, No. 16, Optics Letters, pp. 2309-2311.
Vellekoop, I.M., et al., "Demixing Light Paths Inside Disordered Metamaterials," Jan. 7, 2008, vol. 16, No. 1, Optics Express, pp. 67-80.
U.S. Appl. No. 61/245,580, filed Sep. 24, 2009, McKenna.
U.S. Appl. No. 12/576,377, filed Oct. 9, 2009, Youzhi Li et al.
International Search Report and Written Opinion for PCT Application No. PCT/US2011/043029 dated Oct. 19, 2011; 13 pgs.
Huang, J., et al.; "Low Power Motion Tolerant Pulse Oximetry," Abstracts, A7, p. S103; 2002.
Lang, P., et al.; "Signal Identification and Quality Indicator™ for Motion Resistant Pulse Oximetry," Abstracts, A10, p. S105; 2002.
Hamilton, Patrick S., et al.; "Effect of Adaptive Motion-Artifact Reduction on QRS Detection," Biomedical Instrumentation & Technology, pp. 197-202; 2000.
Kim, J.M., et al.; "Signal Processing Using Fourier & Wavelet Transform," pp. II-310-II-311; 2001.
Odagiri, Y.; "Pulse Wave Measuring Device," Micromechatronics, vol. 42, No. 3, pp. 6-11 (Article in Japanese—contains English summary of article) 1998.
Neumann, R., et al.; "Fourier Artifact suppression Technology Provides Reliable SpO2," Abstracts, A11, p. S105; 2002.

\* cited by examiner

LIGHT FOCUSING CONTINUOUS WAVE PHOTOACOUSTIC SPECTROSCOPY AND ITS APPLICATIONS TO PATIENT MONITORING

BACKGROUND

The present disclosure relates generally to medical devices and, more particularly, to the use of light focusing continuous wave emission in photo-acoustic spectroscopy to analyze vascular network.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Certain monitoring devices, for example, spectroscopy devices, are capable of measuring different physiological parameters, including oxygen saturation, hemoglobin, blood perfusion, and so forth. Spectroscopy devices typically irradiate a patient's tissue with a light. The irradiated region usually encompasses a wide array of blood vessels such as arterioles and capillaries. Absorbance data at known wavelengths of the irradiated light may then be analyzed to provide medical information representative of the physiological region of interest. However, spectroscopic devices may not able to evaluate precise regions of interest, such as individual blood vessels. Accordingly, it would be beneficial to develop systems and methods for monitoring very precise regions of interest, including individual blood vessels and other discrete vascular components.

BRIEF DESCRIPTION OF THE DRAWINGS

Advantages of the disclosure may become apparent upon reading the following detailed description and upon reference to the drawings in which.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain medical contexts it may be desirable to ascertain various localized physiological parameters, such as parameters related to individual blood vessels or other discrete components of the vascular system. Examples of such parameters may include oxygen saturation, hemoglobin concentration, perfusion, and so forth for an individual blood vessel. One approach to measuring such localized parameters is referred to as photoacoustic (PA) spectroscopy.

PA spectroscopy involves a light source suitable for emitting light into a patient tissue such that the emitted light is absorbed by certain constituents of the tissue and/or the vascular system (e.g., blood). The absorbed light energy generates a proportionate increase in kinetic energy of the constituents in the tissue measurement site which in turn results in pressure fluctuations. The pressure fluctuations may be detected in the form of acoustic radiation (e.g., ultrasound) and the acoustic radiation may be used to determine the amount of light absorption, and thus the quantity of the constituents of interest, in the illuminated region. For example, the detected ultrasound energy may be proportional to the optical absorption coefficient of the blood or tissue constituent and the fluence of light at the wavelength of interest at the localized region being measured (e.g., a specific blood vessel). Thus, by emitting a light beam at a wavelength absorbed by constituents in the tissue and/or blood, PA spectroscopy may be used to estimate microcirculatory blood volume, as well as other parameters such as hemoglobin concentration and oxygen saturation (i.e., percentage of oxygen in the blood), at particular measurement sites. Further, it may be possible to create 2-dimensional (2D) as well as 3-dimensional (3D) images of tissue sites, as described in more detail below.

In certain embodiments, increased depth resolution measurements of the constituent may be achieved with the use of a frequency-domain (e.g., Fourier transform) PA spectroscopy system. In frequency-domain (FD) PA spectroscopy, an intensity modulated continuous wave light source may be used that is capable of employing linear frequency modulation (e.g., chirp modulation, sweep modulation) techniques. In linear frequency modulation (LFM), an optical waveform is created with a frequency that increases or decreases with time. Chirp modulation, sometimes referred to as sweep modulation, allows for the use of, for example, a sinusoidal LFM waveform. Techniques such as Fourier transforms may be used to efficiently process the sinusoidal LFM waveforms. Accordingly, the LFM waveform may be employed to irradiate patient tissue, and the ultrasound signals resulting from the irradiation may then be analyzed. A relationship between the time delay of acoustic response and the depth of constituents can be recovered using correlation processing and/or heterodyne signal processing.

One problem that may arise in PA spectroscopy may be attributed to the tendency of the emitted light to diffuse or scatter in the tissue of the patient. As a result, light emitted toward an internal structure or region, such as a blood vessel, may be diffused prior to reaching the region so that amount of light reaching the region is less than desired. Therefore, due to the diffusion of the light, less light may be available to be absorbed by the constituent of interest in the target region, thus reducing the ultrasonic waves generated at the target region of interest, such as a blood vessel. Therefore, the light-to-ultrasound conversion efficiency may be reduced due to the light diffusing properties of the intervening tissue between the surface of the skin and the internal structure or region of interest. In certain embodiments of the present disclosure, the emitted light may be focused on an internal region of interest by spatially modulating the illuminating light to reduce or eliminate the effects of light diffusion. Accordingly, a spatially modulated FD PA spectroscopy system may be capable of more precise measurements of a variety of vessel-specific physiological parameters, which may be desired for many applications.

Figure 1:
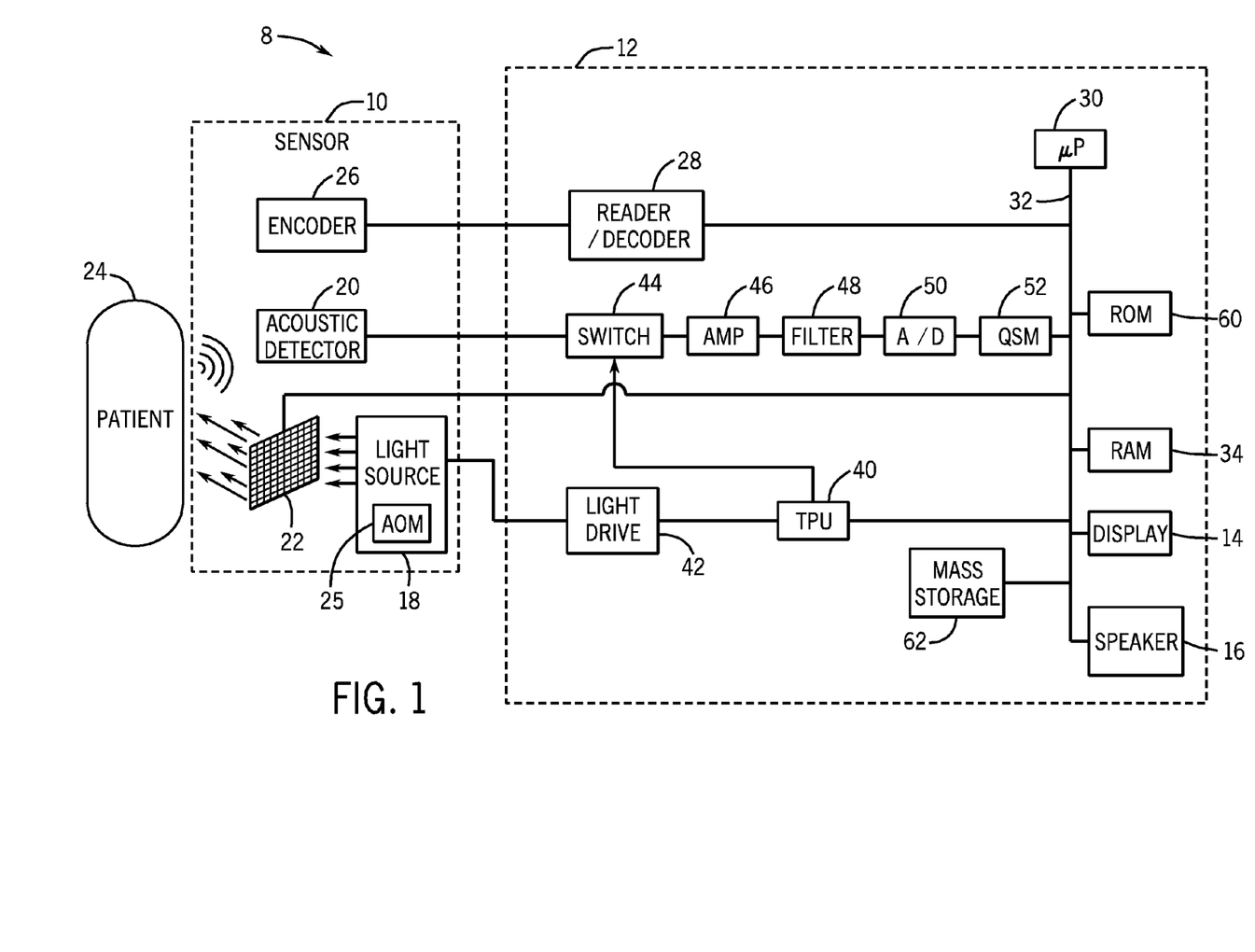
FIG. 1 is a block diagram of a patient monitor and photoacoustic sensor, in accordance with an embodiment.

With this in mind, FIG. 1 depicts a block diagram of a photoacoustic spectroscopy system 8 in accordance with embodiments of the present disclosure. The system 8 includes a photoacoustic spectroscopy sensor 10 and a monitor 12. The sensor 10 may emit spatially modulated light at certain wavelengths into a patient's tissue and may detect acoustic waves (e.g., ultrasound waves) generated in response to the emitted light. The monitor 12 may be capable of calculating physiological characteristics based on signals received from the sensor 10 that correspond to the detected acoustic waves. The monitor 12 may include a display 14 and/or a speaker 16 which may be used to convey information about the calculated physiological characteristics to a user. The sensor 10 may be communicatively coupled to the monitor 12 via a cable or, in some embodiments, via a wireless communication link.

In one embodiment, the sensor 10 may include a light source 18 and an acoustic detector 20, such as an ultrasound transducer. The present discussion generally describes the use of continuous wave (CW) light sources to facilitate explanation. However, it should be appreciated that the photoacoustic sensor 10 may also be adapted for use with other types of light sources, such as pulsed light sources, in other embodiments. In certain embodiments, the light source 18 may be associated with one or more optical fibers for conveying light from one or more light generating components to the tissue site.

The photoacoustic spectroscopy sensor 8 may include a light source 18 and an acoustic detector 20 that may be of any suitable type. For example, in one embodiment the light source 18 may be one, two, or more light emitting components (such as light emitting diodes) adapted to transmit light at one or more specified wavelengths. In certain embodiments, the light source 18 may include a laser diode or a vertical cavity surface emitting laser (VCSEL). The laser diode may be a tunable laser, such that a single diode may be tuned to various wavelengths corresponding to a number of different absorbers of interest in the tissue and blood. That is, the light may be any suitable wavelength or wavelengths (such as a wavelength between about 500 nm to about 1100 nm or between about 600 nm to about 900 nm) that is absorbed by a constituent of interest in the blood or tissue. For example, wavelengths between about 500 nm to about 600 nm, corresponding with green visible light, may be absorbed by deoxyhemoglobin and oxyhemoglobin. In other embodiments, red wavelengths (e.g., about 600 nm to about 700 nm) and infrared or near infrared wavelengths (e.g., about 800 nm to about 1100 nm) may be used. In one embodiment, the selected wavelengths of light may penetrate between 1 mm to 3 cm into the tissue of the patient 24.

An acousto-optic modulator (AOM) 25 may modulate the intensity of the emitted light, for example, by using LFM techniques. The emitted light may be intensity modulated by the AOM 25 or by changes in the driving current of the LED emitting the light. The intensity modulation may result in any suitable frequency, such as from 1 MHz to 10 MHz or more. Accordingly, in one embodiment, the light source 18 may emit LFM chirps at a frequency sweep range approximately from 1 MHz to 5 MHz. In another embodiment, the frequency sweep range may be of approximately 0.5 MHz to 10 MHz. The frequency of the emitted light may be increasing with time during the duration of the chirp. In certain embodiments, the chirp may last approximately 1 second or less and have an associated energy of a 10 mJ or less, such as between 1 µJ to 2 mJ, 1-5 mJ, 1-10 mj. In such an embodiment, the limited duration of the light may prevent heating of the tissue while still emitting light of sufficient energy into the region of interest to generate the desired acoustic shock waves when absorbed by the constituent of interest.

The light emitted by the light source 18 may be spatially modulated, such as via a modulator 22. For example, in one embodiment, the modulator 22 may be a spatial light modulator, such as a Holoeye® LC-R 2500 liquid crystal spatial light modulator. In one such embodiment, the spatial light modulator may have a resolution of 1024×768 pixels or any other suitable pixel resolution. During operation, the pixels of the modulator 22 may be divided into subgroups (such as square or rectangular subarrays or groupings of pixels) and the pixels within a subgroup may generally operate together. For example, the pixels of a modulator 22 may be generally divided into square arrays of 10×10, 20×20, 40×40, or 50×50 pixels. In one embodiment, each subgroup of pixels of the modulator 22 may be operated independently of the other subgroups. The pixels within a subgroup may be operated jointly (i.e., are on or off at the same time) though the subgroups themselves may be operated independently of one another. In this manner, each subgroup of pixels of the modulator 22 may be operated so as to introduce phase differences at different spatial locations within the emitted light. That is, the modulated light that has passed through one subgroup of pixels may be at one phase and that phase may be the same or different than the modulated light that has passed through other subgroups of pixels, i.e., some segments or portions of the modulated light wavefront may be ahead of or behind other portions of the wavefront. In one embodiment, the modulator 22 may be associated with additional optical components (e.g., lenses, reflectors, refraction gradients, polarizers, and so forth) through which the spatially modulated light passes before reaching the tissue of the patient 24.

In one example, the acoustic detector 20 may be one or more ultrasound transducers suitable for detecting ultrasound waves emanating from the tissue in response to the emitted light and for generating a respective optical or electrical signal in response to the ultrasound waves. For example, the acoustic detector 20 may be suitable for measuring the frequency and/or amplitude of the ultrasonic waves, the shape of the ultrasonic waves, and/or the time delay associated with the ultrasonic waves with respect to the light emission that generated the respective waves. In one embodiment an acoustic detector 20 may be an ultrasound transducer employing piezoelectric or capacitive elements to generate an electrical signal in response to acoustic energy emanating from the tissue of the patient 24, i.e., the transducer converts the acoustic energy into an electrical signal.

In one implementation, the acoustic detector 20 may be a low finesse Fabry-Perot interferometer mounted on an optical fiber. In such an embodiment, the incident acoustic waves emanating from the probed tissue modulate the thickness of a thin polymer film. This produces a corresponding intensity modulation of light reflected from the film. Accordingly, the acoustic waves are converted to optical information, which is transmitted through the optical fiber to an upstream optical detector, which may be any suitable detector. In some embodiments, a change in phase of the detected light may be detected via an appropriate interferometry device which generates an electrical signal that may be processed by the monitor 12. The use of a thin film as the acoustic detecting surface allows high sensitivity to be achieved, even for films of micrometer or tens of micrometers in thickness. In one embodiment, the thin film may be a 0.25 mm diameter disk of 50 micrometer thickness polyethylene terepthalate with an at least partially optically reflective (e.g., 40% reflective) aluminum coating on one side and a mirror reflective coating on the other (e.g., 100% reflective) that form the mirrors of the interferometer. The optical fiber may be any suitable fiber, such as a 50 micrometer core silica multimode fiber of numerical aperture 0.1 and an outer diameter of 0.25 mm.

The photoacoustic sensor 10 may include a memory or other data encoding component, depicted in FIG. 1 as an encoder 26. For example, the encoder 26 may be a solid state memory, a resistor, or combination of resistors and/or memory components that may be read or decoded by the monitor 12, such as via reader/decoder 28, to provide the monitor 12 with information about the attached sensor 10. For example, the encoder 26 may encode information about the sensor 10 or its components (such as information about the light source 18 and/or the acoustic detector 20). Such encoded information may include information about the configuration or location of photoacoustic sensor 10, information about the type of lights source(s) 18 present on the sensor 10, information about the wavelengths, light wave frequencies, chirp durations, and/or light wave energies which the light source(s) 18 are capable of emitting, information about the nature of the acoustic detector 20, and so forth. In certain embodiments, the information also includes a reference LFM chirp that was used to generate the actual LFM emitted light. This information may allow the monitor 12 to select appropriate algorithms and/or calibration coefficients for calculating the patient's physiological characteristics, such as the amount or concentration of a constituent of interest in a localized region, such as a blood vessel.

In one implementation, signals from the acoustic detector 20 (and decoded data from the encoder 26, if present) may be transmitted to the monitor 12. The monitor 12 may include data processing circuitry (such as one or more processors 30, application specific integrated circuits (ASICS), or so forth) coupled to an internal bus 32. Also connected to the bus 32 may be a RAM memory 34, a speaker 16 and/or a display 14. In one embodiment, a time processing unit (TPU) 40 may provide timing control signals to light drive circuitry 42, which controls operation of the light source 18, such as to control when, for how long, and/or how frequently the light source 18 is activated, and if multiple light sources are used, the multiplexed timing for the different light sources.

The TPU 40 may also control or contribute to operation of the acoustic detector 20 such that timing information for data acquired using the acoustic detector 20 may be obtained. Such timing information may be used in interpreting the shock wave data and/or in generating physiological information of interest from such acoustic data. For example, the timing of the acoustic data acquired using the acoustic detector 20 may be associated with the light emission profile of the light source 18 during data acquisition. Likewise, in one embodiment, data acquisition by the acoustic detector 20 may be gated, such as via a switching circuit 44, to account for differing aspects of light emission. For example, operation of the switching circuit 44 may allow for separate or discrete acquisition of data that corresponds to different respective wavelengths of light emitted at different times.

The received signal from the acoustic detector 20 may be amplified (such as via amplifier 46), may be filtered (such as via filter 48), and/or may be digitized if initially analog (such as via an analog-to-digital converter 50). The digital data may be provided directly to the processor 30, may be stored in the RAM 34, and/or may be stored in a queued serial module (QSM) 52 prior to being downloaded to RAM 34 as QSM 52 fills up. In one embodiment, there may be separate, parallel paths for separate amplifiers, filters, and/or A/D converters provided for different respective light wavelengths or spectra used to generate the acoustic data.

The data processing circuitry (such as processor 30) may derive one or more physiological characteristics based on data generated by the photoacoustic sensor 12. For example, based at least in part upon data received from the acoustic detector 20, the processor 30 may calculate the amount or concentration of a constituent of interest in a localized region of tissue or blood using various algorithms. In certain embodiments, these algorithms may use coefficients, which may be empirically determined, that relate the detected acoustic shock waves generated in response to emitted light waves at a particular wavelength or wavelengths to a given concentration or quantity of a constituent of interest within a localized region. Further, 2D and 3D images may be created by analyzing the ultrasound signals. Such analysis may incorporate techniques that can extract the image based on, for example, the observation that the magnitude of the ultrasonic signal is proportional to the energy deposited by the emitted light, and the further observation that different types of constituents absorb light at different wavelengths. In addition, in one embodiment the data processing circuitry (such as processor 30) may communicate with the TPU 40 and/or the light drive 42 to spatially modulate the wave front of light emitted by the light source 18 based on one or more algorithms, as discussed herein.

In one embodiment, processor 30 may access and execute coded instructions, such as for implementing the algorithms discussed herein, from one or more storage components of the monitor 12, such as the RAM 34, a ROM 60, and/or the mass storage 62. Additionally, the RAM 34, ROM 60, and/or the mass storage 62 may serve as data repositories for information such as templates for LFM reference chirps, coefficient curves, and so forth. For example, code encoding executable algorithms may be stored in the ROM 60 or mass storage device 62 (such as a magnetic or solid state hard drive or memory or an optical disk or memory) and accessed and operated according to processor 30 instructions using stored data. Such algorithms, when executed and provided with data from the sensor 10, may calculate a physiological characteristic as discussed herein (such as the type, concentration, and/or amount of a constituent of interest). Once calculated, the physiological characteristic may be displayed on the display 14 for a caregiver to monitor or review.

Figure 2:
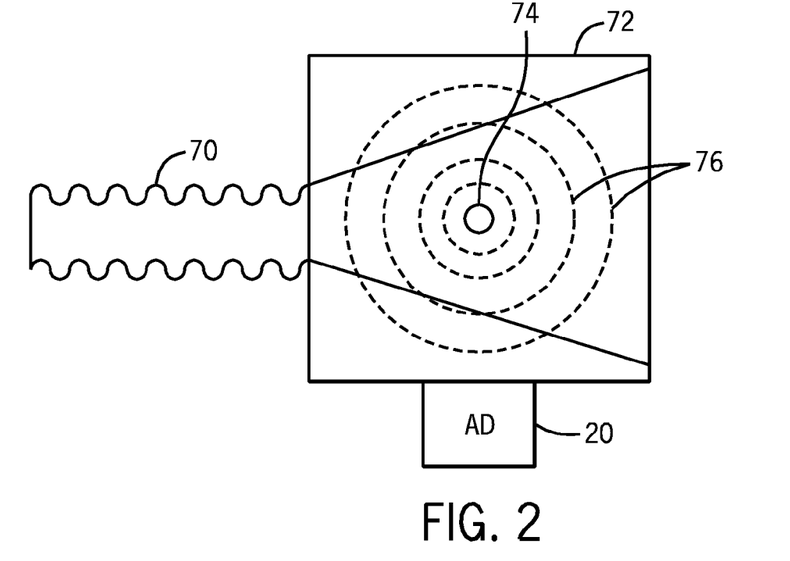
FIG. 2 depicts a photoacoustic measurement in accordance with an embodiment.

With the foregoing system discussion in mind, light emitted by the light source 18 of the photoacoustic sensor 10 may be used to generate acoustic signals in proportion the amount of an absorber (e.g., a constituent of interest) in a targeted localized region. However, as noted above, the emitted light may be scattered upon entering the tissue, with the amount of scatter or dispersion increasing as the light penetrates deeper into the tissue. Thus, for localized regions or structures of interest, such as blood vessels, the greater the depth of such vessels beneath the tissue surface, the greater the dispersion of the emitted light before reaching the localized region or structure. For example, referring to FIG. 2, a CW light 70 may be generated by using intensity modulation techniques such as linear frequency modulation (LFM). In LFM, the CW light 70 may use LFM coding, such as a reference LFM signal that increases its frequency over time. The CW light 70 may thus incorporate the LFM signal to produce a corresponding light wave with a linearly increasing frequency. The CW light 70 may then be emitted into a tissue 72, which results in acoustic waves. LFM processing techniques such as correlation processing and/or heterodyne signal processing may be applied to the acoustic wave response as describe in more detail below with respect to FIG. 3, to determine the measurements of interest. However, the CW light 70 may begin to disperse upon entering the tissue 72. As a result, the intensity and/or fluence of the emitted light incident upon the localized region of interest 74, such as blood vessel, may be reduced, resulting in less absorption by the constituent of interest within the localized region 74 and proportionately less energetic acoustic waves 76 being generated. This may yield a relatively low strength signal at the acoustic detector 20 relative to the noise (i.e., low signal-to-noise ratio) associated with the measurement.

Figure 3:
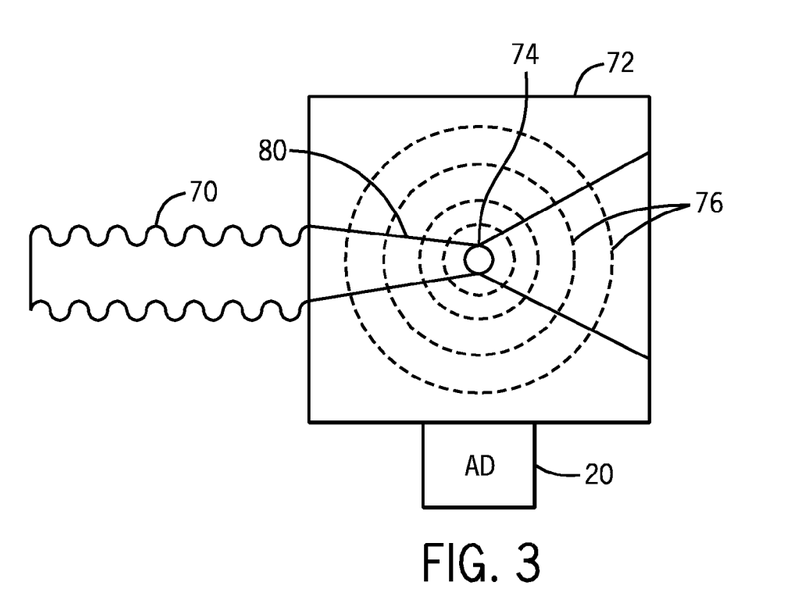
FIG. 3 depicts a focused photoacoustic measurement in accordance with an embodiment.

Turning to FIG. 3, in one embodiment, the strength of the measured signal may be increased by focusing the CW light 70, such as the LFM encoded CW light, on the region of interest 74, as denoted by focused beam 80. Such focusing may result in less dispersal or scattering of the light prior to reaching the region of interest 74 and correspondingly greater intensity and/or fluence of the light at the region of interest 74. As a result more absorption of light by the constituent of interest may occur in the region of interest 74, yielding proportionately more energetic acoustic waves 76 with a corresponding higher signal-to-noise ratio at the acoustic detector 20.

The CW light 70 may be intensity modulated by the AOM 22, for example, by using LFM techniques. The CW light 70 may then be focused on one or more concurrent focal points by spatially modulating the CW light 70 to yield an inverse wave diffusion effect upon entering the scattering medium, i.e., the patient tissue. In effect, multi-path interference may be employed so that the scattering process itself focuses the emitted light onto the desired focal point or points. In particular, to the extent that at any given time the disorder in a medium is fixed or determinable, light scattering in the medium is deterministic and this knowledge may be utilized to modulate the emitted light such that the resulting scatter in the medium results in the light being concentrated or focused on a desired region of interest.

The CW light 70 may be further spatially modulated using a liquid crystal phase modulator or other suitable modulator 22. For example, to the extent that a continuous light wave may have a planar wavefront, a spatially modulated light wave, as discussed herein, may have a wavefront that is not planar and instead may be shaped by breaking the wavefront up into numerous sub-planes (e.g., square or rectangular segments) that are not all at the same phase, such that different portions of the wavefront reach the tissue surface at different times. The operation of the modulator 22 may be updated or iterated based upon feedback from the acoustic detector 20. For example, in one embodiment the signals generated by the acoustic detector 20 may be processed by a processor 30 which may in turn evaluate the processed signal in accordance with one or more algorithms or thresholds (such as a signal-to-noise threshold) and adjust operation of the modulator 22 accordingly. In one embodiment adaptive learning algorithms or other suitable analysis algorithms (e.g., neural networks, genetic algorithms, and so forth) may be employed to evaluate the processed signal and to make adjustments to the modulation.

In one example, an algorithm may be stored in the memory 34 and executed by the processor 30 to generate the inverse diffusion wavefront. One such algorithm may utilize the linearity of the scattering process in the tissue to generate the diffusion wavefront. For example, in one embodiment, the inverse diffusion wavefront may be generated in accordance with the equation:

$$E_m = \sum_{n=1}^{N} t_{mn} A_n e^{i\phi_n} \quad (1)$$

where $E_m$ is the linear combination of the fields coming from N different wavefront segments generated by the modulator 22, $A_n$ is the amplitude of the light reflected from segment n, $\phi_n$ is the phase of the light reflected from segment n, and $t_{mn}$ is the scattering in the sample and propagation through the optical system. In accordance with such an equation, the magnitude of $E_m$ may be maximized when all terms are in phase. The optimal phase for a segment, n, of the light wavefront at a given time may be determined by cycling its phase from 0 to $2\pi$ while the phase of other segments is held constant. This process may then be repeated for each segment. The optimal phase for each segment for which the target intensity is highest may then be stored. Once the optimized phase is known for each segment of the wavefront, the modulator 22 may be programmed based on the stored values such that differential activation of the pixels or subgroups of pixels defined for the modulator 22 (such as for a liquid crystal phase modulator) spatially modulates the light incident upon the modulator 22. That is, differential adjustment of the opacity of elements defined by the modulator 22 (such as square or rectangular groupings of pixels of a liquid crystal element) may yield a light with a wavefront in which different segments or portions of the wavefront are out of phase, i.e., staggered with respect to one another. When the resulting spatially modulated light is transmitted through the tissue, the contributions attributable to each modulated portion of the wavefront of the light may constructively interfere with one another to yield the desired light intensity at the localized region of interest, as depicted in FIG. 3.

While the preceding describes one implementation for generating a spatially modulated wavefront, such a wavefront may also be generated by an algorithm stored in the memory 34 and executed by the processor 30 that models the optical field E at a point $r_b$ within a medium in accordance with:

$$E(r_b) = \int g(r_b, r_a)\phi(r_a) d^3 r_a \quad (2)$$

in which g is Green's function describing propagation from $\phi(r_a)$ to point $r_b$. In an embodiment, each segment of the phase modulator is treated as a planar source having amplitude A and phase $\phi$. If the phase modulator is assumed to be illuminated uniformly, the amplitudes A at each segment may be assumed to be equal. By integrating the surface area S of each of the N segments, Equation (2) may be represented as:

$$E(r_b) = \sum_{a}^{N} \int_{S_a} g(r_b, r_a) d^2 r_a A e^{i\phi_a} \quad (3)$$

which in turn yields $$E(r_b) = A \sum_{a}^{N} g_{ba} e^{i\phi_a}. \quad (4)$$

Changing the phase of a segment a of the phase modulator 22 while holding the phase of other segments unchanged causes the intensity I at point $r_b$ to respond in accordance with:

$$I(r_b) \equiv |E(r_b)|^2 = I_{0b} + 2ARe(E^*_{b\bar{a}} g_{ba} e^{i\phi_a}) \quad (5)$$

in which:

$$I_{0b} \equiv |E_{b\bar{a}}|^2 + A^2|g_{ba}|^2 \quad (6)$$

and $$E_{b\bar{a}} \equiv A \sum_{a' \neq a}^{N} g_{ba'} e^{i\phi'_a} \approx E(r_b). \quad (7)$$

Where the number of segments N is large $E_{b\bar{a}} \approx E(r_b)$ and is therefore essentially the same across all segments. By analyzing each segment a in this manner, the coefficients $g_{ba}$ may be measured up to an unknown common prefactor $E(r_b)$. By determining the coefficients $g_{ba}$, the optical field at point $r_b$ (e.g., $E(r_b)$) may be maximized by setting $\phi_a$ equal to $-\arg(g_{ba})$ for each of the segments. This combination of segment phases thus can yield an aggregate light intensity maximum at the region of interest:

$$E_{max}(r_b) = A \sum_{a}^{N} |g_{ba}| \quad (8)$$

in which the different light channels associated with each channel will undergo constructive interference to reach the region of interest.

The amount of intensity enhancement observed at the localized region 74 may be related to the numbers of segments or regions into which the wavefront of the CW light 70 is broken. To the extent that the constants $t_{mn}$ are statistically independent and obey a circular Gaussian distribution, the expected enhancement, η, may be represented as:

$$\eta = \frac{\pi}{4}(N - 1) + 1 \quad (9)$$

where η is the ratio between the enhanced light intensity at the region of interest and the average light intensity at the region of interest prior to enhancement.

In one example, correlation processing (e.g., matched filter compression) may be used to process the LFM responses received by the acoustic detector 20. Match filter detection allows the matching of the peaks and valleys of the reference signal (e.g., LFM reference chirp) with the corresponding detected acoustic signal so as to reduce or eliminate noise. Matched filter detection of a signal s(t) is based on the observation that the highest signal-to-noise ratio is achieved at the time $t=t_0$ if the filter frequency response H(w) is equal to the complex subjugate of the signal spectrum:

$$H(w) = S^*(w) e^{-iwt_0} \quad (10)$$

where the signal output of the filter with spectral response (10) is given by:

$$s_{out}(t) = \frac{1}{2\pi} \int_{-\infty}^{\infty} S(w) H(w) e^{iwt} dw = B_s(t - t_0) \quad (11)$$

where $B_s(t-t_0)$ is the correlation function of the signal s(t). Accordingly, the received acoustic response can be correlated with the reference LFM signal (e.g., chirp reference) to compute $B_s(t-t_0)$. In certain embodiments, fast Fourier transform (FFT) techniques may be used to compute the correlation function in the frequency domain and transform back to the time domain using the inverse FFT. The depth of various photoacoustic sources (e.g., discrete vascular components) may be determined based on the speed of propagation and the time of the observed acoustic responses to the emitted light. By varying the wavelengths used for observation, various different types of constituents may be derived based on the observation that different types of constituents absorb light at different wavelengths. Accordingly, a 2D image of the observed area may be constructed by using the derived depths, the constituent types, the constituent amount, and or the constituent concentration found at each depth. A 3D image may be constructed by layering a set of 2D images, each layer corresponding to a different tissue depth.

In another embodiment, heterodyne mixing with coherent detection may be used to decode the LFM responses received by the acoustic detector 20. This technique is based on heterodyne mixing of LFM waveforms and coherent detection of the down-shifted signal at the single frequency specified by the internally generated LFM reference signal. The signal detected by the acoustic detector 20 contains the chirp $f(t) = f_0 + \beta(t-t_0)$ delayed by the time $t_0 = z/c_a$ where β is the frequency f sweep rate, z is the tissue depth, and $c_a$ is the speed of sound in tissue. The delayed response signal s(t) is given by:

$$s(t) = A_s \exp\left\{i2\pi\left[(f_0 - \beta t_0)t + \beta\frac{t^2}{2}\right]\right\} \quad (12)$$

where $A_s$ is the complex amplitude and is assumed to be a constant within the chirp bandwidth. Computing the product s(t)·r(t) where r(t) is the chirp reference signal, and removing the sum frequency components using, for example, a low-pass filter, gives the down-shifted signal V(t):

$$V(t) = <s(t) \cdot r(t)> \propto A_s \exp\left(i2\pi\beta\frac{z}{c_a}t\right) \quad (13)$$

Equation 13 shows that for the specific depth z, the signal V(t) contains the frequency component $f_z = \beta z/c_a$. Therefore, heterodyne mixing provides a direct relationship between the spectrum of the down-shifted signal and the depth of the photoacoustic sources. Any suitable coherent lock-in algorithm may be used to suppress all signals at the frequencies $f \neq f_r$. Setting the reference frequency $f_r$ is equivalent to selecting a specific depth for observation. As mentioned above, a 2D image of the observed area may be constructed by selecting a specific depth for observation and deriving the constituent types found at each depth. Similarly, a 3D image may be constructed by layering a set of 2D images with each layer corresponding to a different tissue depth.

Thus, in accordance with the present disclosure, emitted light may be intensity and spatially modulated so as to converge on a region of interest within an otherwise scattering medium (e.g., tissue). In the context of photoacoustic spectroscopy, such convergence may be used to increase the fluence of light at the internal region of interest (e.g., light absorber) and to, thereby, improve the signal-to-noise ratio of the generated acoustic signal. That is, focusing the emitted light on the internal region (such as by spatial modulation of the respective CW light wavefronts) generates a stronger acoustic signal, thereby improving the measurement process. Such techniques allow for precise measurements in individual vasocirculatory structures. For example hemoglobin concentration and oxygen saturation (i.e., percentage of oxygen in the blood) measurements may now be derived in localized regions of interest. The optical absorption spectra of oxygenated hemoglobin ($HbO_2$) and deoxygenated hemoglobin (Hb) may be used to determine precise quantities of these two chromophores in the area being observed by irradiating the area with light near certain wavelengths such as 660 nm and 900 nm. The chromophores preferentially absorb light at certain wavelengths resulting in enhanced or reduced ultrasonic responses based on which wavelength is currently used to irradiate the tissue. The resulting ultrasonic responses may be analyzed to measure hemoglobin concentration as well as oxygen saturation in arterial and venous conduits. Such measurements allow for determination of conditions such as anemia, iron deficiency, low or high blood oxygenation, and so forth.

Imaging modalities may also be employed that allow for enhanced detail and image resolution of the tissue site under observation. Indeed, detailed in vivo 2D and 3D imaging may be created by deriving an image based on the type, amount concentration, and/or the location of the various tissue constituents observed by the photoacoustic spectroscopy system 8. The signals resulting from such observations may be processed by the techniques disclosed above, such as the algorithmic techniques, to derive an image corresponding to the image of the area under observation. Such imaging may be useful for capillary mapping, skin melanoma detection, and so forth. It is thus possible to observe the micro circulation of blood among individual arterioles and venules, thus enabling the characterization of blood flow and tissue perfusion (e.g., hydrostatic pressure measurements, osmotic pressure measurements) at a capillary level. Additionally, soft brain tissues having different optical absorption properties may be observed by the techniques disclosed herein. For example, an absorption contrast and resulting ultrasonic response between a lesion area and a healthy area may be significantly different. Accordingly, a lesion area may be identified and imaged during in vivo examination of brain tissue using the photoacoustic spectroscopy system 8.

Figure 4:
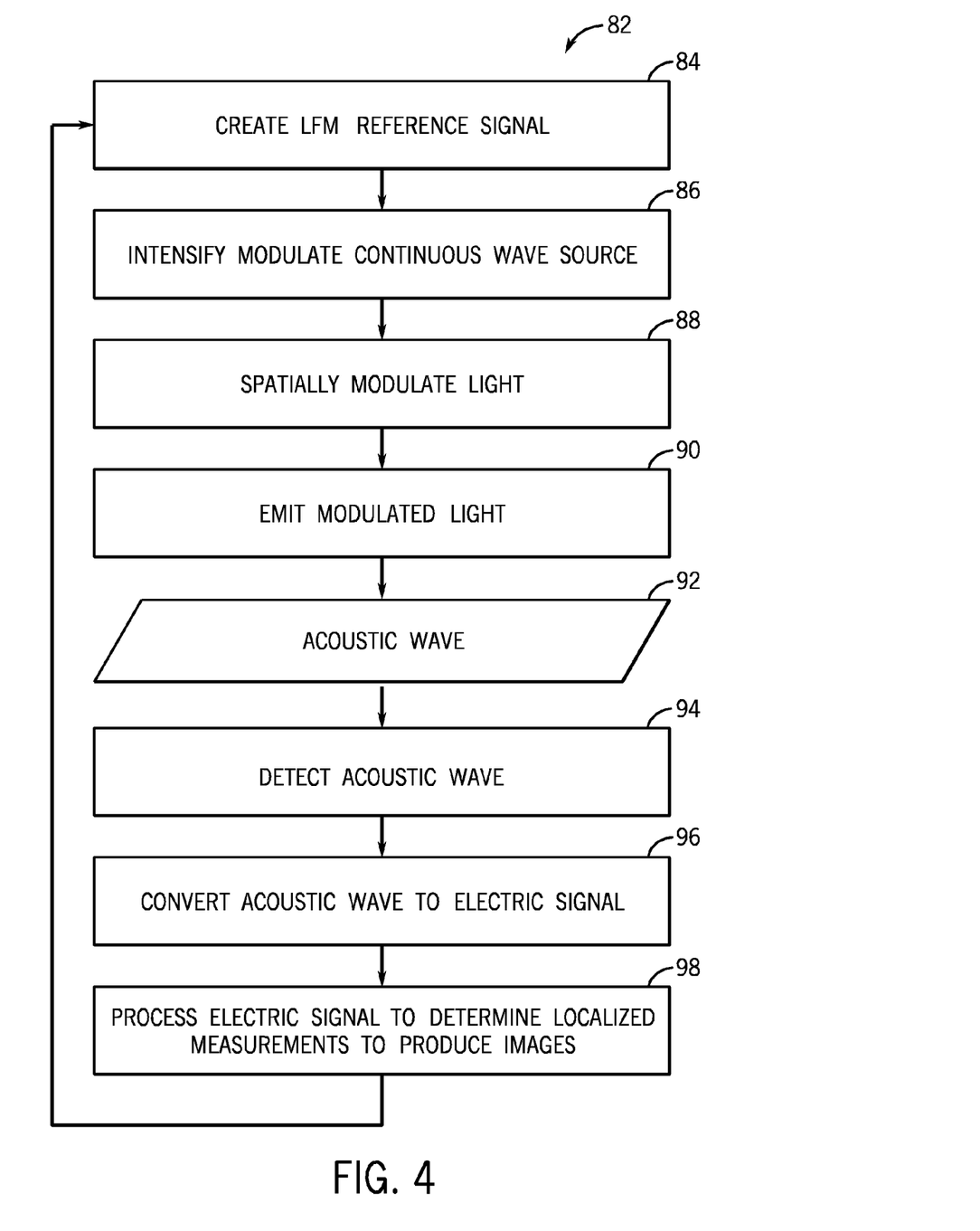
FIG. 4 depicts a flowchart of a method for observing localized regions of interest.

Turning to FIG. 4, the figure is a flowchart of a logic 82 that may be employed to measure very precise regions of interest in a tissue. The LFM reference chirp (i.e., reference signal) may be created, for example by retrieving a template chirp stored in ROM 60 or by using a function generator (block 84). In certain embodiments, the AOM 25 may use the LFM reference chirp to drive a laser so as to emit an intensity modulated continuous wave light with frequencies corresponding to those of the LFM reference chirp (block 86). In these embodiments, the modulation may include an intensity modulation, that is, the optical power of the laser may be varied in accordance with the variations of the LFM signal. The emitted light may then be redirected into a spatial light modulator for further focusing through spatial modulation (block 88). The spatial light modulator is capable of altering the wavefront of the incident light as described above in relation to FIG. 3 such that the wavefront may be broken up into numerous sub-planes that are not all at the same phase. The spatially modulated light may then be emitted onto a tissue sample (block 90).

The light incident upon the tissue sample may encounter a light absorber and experience kinetic energy activity that results in ultrasonic shock waves. The resultant ultrasonic shockwaves will generate acoustic waves 92 that can be detected, for example, by the acoustic detector 20 (block 94). The acoustic detector 20 is capable of converting the detected acoustic waves into electric signals (block 96). In certain embodiments, the electronic signals are processed by a variety of algorithms as described above so as to determine a concentration or quantity measure of light absorbers within a localized region of the tissue (block 98). As mentioned previously, the algorithms are capable of using a variety of spatial modulation intensity enhancement techniques to observe the localized region. Similarly, LFM processing techniques may be employed to process the LFM components of the signal. The processed signal may be used to determine localized measurements of certain physiologic parameters such as hemoglobin concentration and oxygen saturation. Other measurements may be obtained based on microcirculatory observations, such as hydrostatic pressure measurements and osmotic pressure measurements. Further, imaging modalities may be employed to produce in vivo images such as capillary maps, tissue maps, brain lesion images, and so forth, based on, for example, differing absorption contrasts among tissue regions. Indeed, the techniques disclosed herein allow for very precise imaging of tissue as well as for obtaining measurements of highly localized regions of interest. The logic 82 may then iteratively modulate the emitted light and process the resulting signal so as to continuously observe the region of interest, as illustrated.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may be applied to various types of medical devices and monitors, as well as to electronic device in general. Rather, the various embodiments may cover all modifications, equivalents, and alternatives falling within the spirit and scope of the disclosure as defined by the following appended claims.

What is claimed is:

1. A photoacoustic system, comprising:
   a light emitting component configured to continuously emit one or more wavelengths of light;
   a first light modulating component configured to intensity modulate the light emitted by the light emitting component;
   a second light modulating component configured to spatially phase-modulate light emitted by the first light modulating component, wherein the system is configured to direct the spatially phase-modulated light into a tissue of a patient;
   an acoustic detector configured to detect acoustic energy generated in the tissue in response to the spatially phase-modulated light; and
   a processor configured to determine a quantity measure of a physiologic parameter of the patient and to adjust the second light modulating component based on the acoustic energy detected by the acoustic detector.

2. The photoacoustic system of claim 1, wherein one or more of the light emitting component, the first light modulating component, the second light modulating component, the acoustic detector, or the processor are provided in a sensor body.

3. The photoacoustic system of claim 1, comprising a monitor communicatively coupled with one or more of the light emitting component, the first light modulating component, the second light modulating component, or the acoustic detector, wherein the processor is provided in the monitor and the monitor is configured to control the light emitting component, the first light modulating component, the second light modulating component, or the acoustic detector.

4. The photoacoustic system of claim 1, wherein the intensity modulation of the light comprises linear frequency modulation (LFM).

5. The photoacoustic system of claim 1, wherein the physiologic parameter comprises a hemoglobin concentration or an oxygen saturation.

6. The photoacoustic system of claim 1, wherein the light emitting component comprises one or more light emitting diodes, one or more laser diodes, or a vertical cavity surface emitting laser.

7. The photoacoustic system of claim 1, wherein the acoustic detector comprises one or more of an ultrasound transducer or an interferometer.

8. The photoacoustic system of claim 1, wherein the first light modulating component comprises an acousto-optic modulator.

9. The photoacoustic system of claim 1, wherein the second light modulating component comprises a liquid crystal spatial light modulator.

10. The photoacoustic system of claim 9, wherein the second modulator comprises a plurality of subgroups of pixels.

11. The photoacoustic system of claim 10, wherein each subgroup of pixels operates independently of the other subgroups.

12. The photoacoustic system of claim 1, wherein adjusting the second light modulator comprises evaluating a signal generated by the acoustic detector in response to the acoustic energy with an algorithm.

13. The photoacoustic system of claim 12, wherein the algorithm comprises Green's function.

14. The photoacoustic system of claim 1, wherein adjusting the second light modulator comprises evaluating a signal generated in response to the acoustic energy with a signal-to-noise threshold.

15. A photoacoustic system, comprising:
a continuous wave light source configured to emit continuous wave light at one or more wavelengths of light;
a first modulator configured to intensity modulate the continuous wave light;
a second modulator configured to modulate wavefronts associated with the continuous wave light modulated by the first modulator, such that each wavefront exhibits different phases at different locations, wherein the wavefronts are configured to be directed into a tissue;
an acoustic detector configured to generate an electrical signal in response to acoustic waves generated in the tissue in response to the emitted continuous wave light; and
a processor configured to determine a quantity measure of a physiologic parameter and to adjust the second the second modulator based on the electrical signal generated by the acoustic detector.

16. The photoacoustic system of claim 15, wherein the one or more respective wavelengths are between approximately 500 nm to approximately 1,100 nm.

17. The photoacoustic system of claim 15, wherein the processor is configured to determine a concentration or a type of an absorber based on the electrical signal generated by the acoustic detector.

18. The photoacoustic system of claim 15, wherein the intensity modulation of the light comprises linear frequency modulation (LFM).

19. The photoacoustic system of claim 18, wherein the first modulator comprises an acousto-optic modulator or circuit configured to change the driving current of the light source.

20. The system of claim 15, wherein the processor is configured to estimate a signal-to-noise ratio of the electrical signal and to adjust an operating characteristic of the second light modulating component based on the signal-to-noise ratio.

21. The system of claim 20, wherein the processor is configured to use adaptive learning algorithms to adjust the operating characteristic of the second light modulating component based on the signal-to-noise ratio.

22. The system of claim 15, wherein each of the wavefronts associated with the continuous wave light comprise a plurality of segments, and wherein the processor is configured to determine a target phase for each segment of the plurality of segments by cycling a phase of each segment individually and identifying the target phase that corresponds to the maximum intensity, storing the target phase for each segment in a memory of the system, and controlling the second modulator to modulate each of the wavefronts based on the target phase for each segment.

23. A method for processing acoustic signals, comprising:
using a processor to perform the steps of:
creating an intensity modulated chirp of continuous wave light;
spatially phase-modulating the continuous wave light chirp without changing an intensity profile of the continuous wave light chirp;
emitting the spatially phase-modulated light chirp towards a tissue of a patient;
detecting one or more acoustic waves generated within the tissue in response to the spatially phase-modulated light chirp;
generating a signal corresponding to the one or more acoustic waves;
processing the signal to generate a quantity measure of one or more physiological parameters related to the presence of a light absorber within the tissue; and
adjusting the spatially phase-modulated light chirp based on the signal and a signal-to-noise threshold.

24. The method of claim 23, wherein spatially modulating the continuous wave light chirp comprises altering respective wavefronts associated with the light chirp such that each respective wavefront comprises different regions at different phases.

25. The method of claim 23, comprising separately processing the signal to generate one or more images related to the presence of the light absorber within the tissue.

* * * * *